United States Patent
Waterman et al.

[11] 3,961,246
[45] June 1, 1976

[54] CAPACITANCE METHOD OF MONITORING INSULATION DRYNESS OF AN ELECTRICAL INDUCTION APPARATUS

[75] Inventors: Michael W. Waterman, Milwaukee; Samuel L. Foster, Eagle, both of Wis.

[73] Assignee: Allis-Chalmers Corporation, Milwaukee, Wis.

[22] Filed: Nov. 7, 1974

[21] Appl. No.: 521,743

[52] U.S. Cl. .............................. 324/54; 317/157.62; 324/61 R
[51] Int. Cl.² .................. G01R 27/26; G01R 31/12
[58] Field of Search ............ 324/54, 55, 61 R, 61 P; 317/157.62

[56] References Cited
UNITED STATES PATENTS

| | | | |
|---|---|---|---|
| 1,371,378 | 3/1921 | Klauber | 324/54 |
| 2,679,026 | 5/1954 | Frakes | 324/54 |
| 2,899,635 | 8/1959 | Yardney | 324/61 R |
| 2,976,720 | 3/1961 | Callahan | 324/61 R X |
| 2,985,826 | 5/1961 | Fluegel | 324/61 R |
| 3,753,092 | 8/1973 | Ludlow et al. | 324/61 R |

*Primary Examiner*—Gerard R. Strecker
*Attorney, Agent, or Firm*—Robert C. Jones

[57] ABSTRACT

Model insulation structure representative of the most critical insulation in a stationary induction apparatus is placed in the bottom of the oil tank and is provided with spaced conductive electrodes forming a capacitor having sufficient capacitance for measuring the dissipation or power factor of the insulation.

8 Claims, 4 Drawing Figures

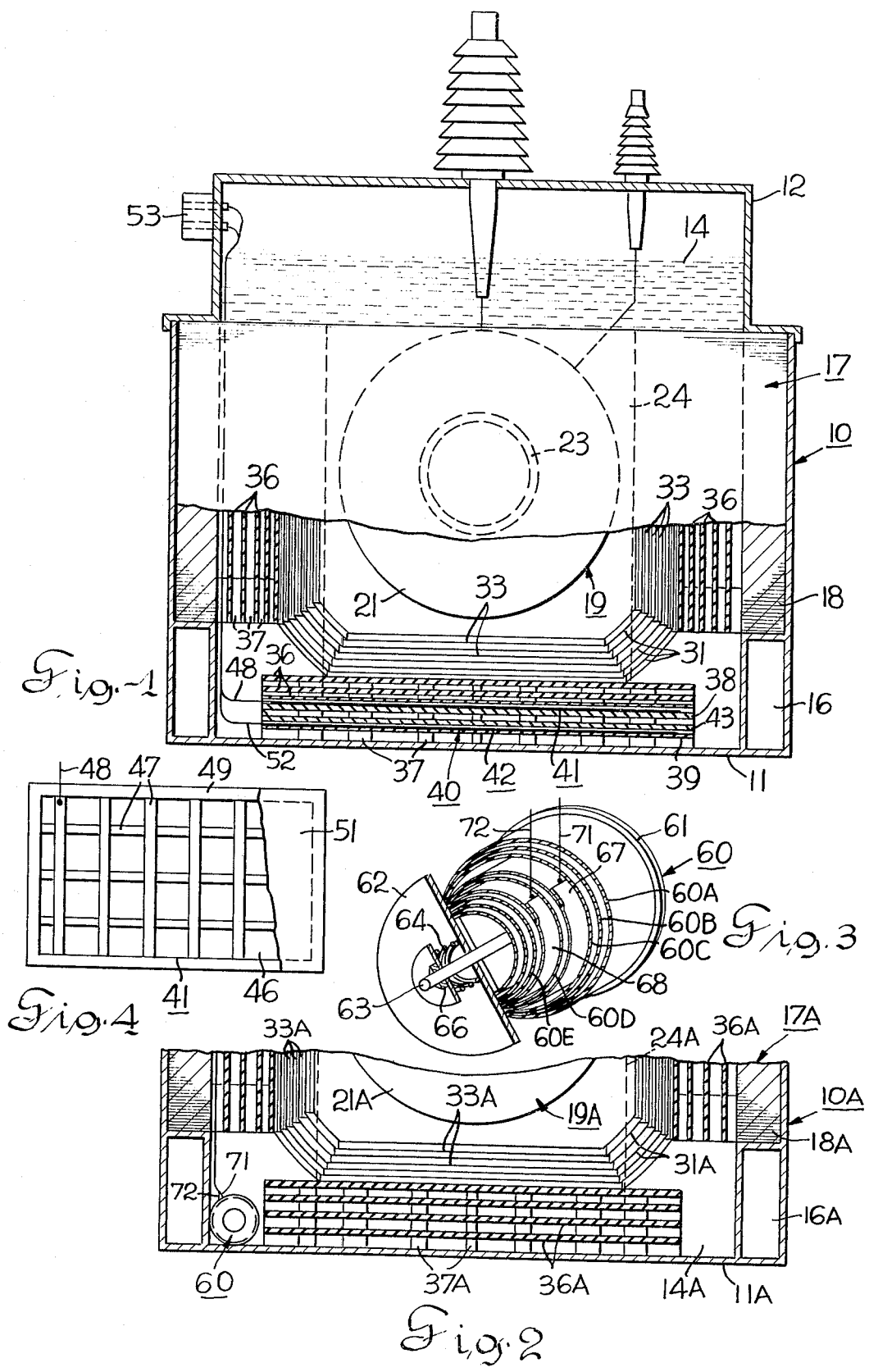

CAPACITANCE METHOD OF MONITORING INSULATION DRYNESS OF AN ELECTRICAL INDUCTION APPARATUS

BACKGROUND OF THE INVENTION

Direct measurement of winding insulation does not provide a good indication of the moisture content of insulation in stationary induction apparatus, particularly those types immersed in oil for cooling purposes, and more particularly, with oil immersed induction apparatus with reduced insulation at the neutral. This is true because if the neutral insulation space is small, the stationary induction apparatus will have a large capacitance from winding to tank which substantially affects the determination of the dissipation or power factor. Thus, the condition of the insulation at the high voltage end of the winding, which is the important factor, will be masked by the large neutral end capacitance. This is especially true if high dissipation or power factor materials such as impregnated and laminated paper are used in the mechanical structure. In this arrangement when making field measurements, the power system must be disconnected from the induction apparatus because of the parallel capacitance of lightning arrestors, insulators, etc.

Another method to determine moisture content of stationary induction apparatus insulation is the measurement of the gas space dew point. The gas space dew point method to determine the moisture content requires a careful technique. Usually, electronic probes are used with the dew point method and these probes must be accurately calibrated and are also easily damaged. In addition, a long period of constant ambient and operating conditions is required to insure that there is equilibrium between the moisture content of the insulation, oil and gas space.

Still another method that is used to determine the moisture content of stationary induction apparatus insulation is the laboratory analysis of the moisture content of the oil. However, with this method, the sampling technique as well as the analysis is critical to a point that field personnel cannot normally perform the sampling nor the analyzing.

In addition, all of the above methods of determining the moisture content in stationary induction apparatus do not indicate the localized concentration of moisture in the insulation which is usually experienced in the lower or bottom portion of the oil tank.

SUMMARY OF THE INVENTION

The present invention is an improved method and means for determining the insulation dryness of high voltage stationary induction apparatus such as shunt reactors and transformers. With the present invention, representative insulating structure having electrodes spaced by at least one layer of the insulation to form a capacitor is placed in the bottom of the oil tank and leads are connected and brought out to the exterior of the tank for measuring the dissipation or power factor of the insulation. The model insulation is arranged to be representative of the most critical insulation in the induction apparatus and provide sufficient capacitance for accurate measurements.

It is a general object of the present invention to provide an improved method for determining the insulation dryness of high voltage stationary induction apparatus.

Another object of the present invention is to provide a method and means for measuring the dissipation or power factor of paper insulation at the high voltage end of the windings of a stationary induction apparatus which will not be masked by the large neutral end capacitance.

Still another object of the present invention is to provide a method and means for measuring the dissipation or power factor of the insulation of a stationary induction apparatus without the necessity of disconnecting the induction apparatus from the power system.

Yet another object of the present invention is to provide a method and means for measuring the dissipation or power factor of the insulation of stationary induction apparatus which provides sufficient capacitance for accurate measurement.

A still further object of the present invention is to provide a method and means for determining the moisture content of the insulation of a stationary induction apparatus.

DESCRIPTION OF THE DRAWINGS

FIG. 1 is a view in elevation of a single phase stationary induction apparatus in which the invention has been incorporated, with parts broken away to show some of the insulation thereof;

FIG. 2 is a fragmentary view in section of the lower portion of a stationary induction apparatus showing a modification of the invention of FIG. 1;

FIG. 3 is an enlarged isometric view of the moisture sensing means shown in FIG. 2; and, FIG. 4 is a plan view of an electrode showing the collectors on the carbon paper and the backing paper to reinforce the electrodes.

DESCRIPTION OF THE INVENTION

Referring to the drawings, a shunt reactor 10 embodying the invention may be used in each phase of a multiphase extra high voltage electrical power transmission system. The reactor 10 includes a tank 11 having a cover 12 and filled with a dielectric cooling and insulating oil 14. Tank 11 is provided with an oil circulating manifold 16 which extends around the entire side walls of the tank 11. The manifold 16 may also serve to support a rectangular magnetic yoke, or core 17 having magnetic steel laminations 18 disposed in horizontal planes and parallel to the axis of a cylindrical reactor coil 19 positioned within the window of the core 17 so that the axial ends of the coil 19 are closely adjacent the end portions of the magnetic yoke.

The coil 19 has a nonmagnetic core and comprises a plurality of electrically connected but axially spaced coaxial pancake windings 21, one of which is shown. A typical shunt reactor coil 19 may have approximately 80 pancake windings 21. The pancake windings 21 are supported on a tube 23 of an insulating material having a high dielectric strength. The ends of supporting tube 23 extend beyond the pancake windings 21 and into suitable openings provided in insulating headboards 24, one of which is shown.

Planar insulating washers 31 are disposed between the pancake windings 21 which may be circular and/or rectanglar and herein depicted as being rectangular having clipped corners. For a more detailed description of the construction and arrangement of the internal structure, reference may be had to U.S. Pat. No. 3,362,001 assigned to the same assignee as the subject application. The washers 31 are maintained apart by means of radially extending spacer sticks (not shown) to provide cooling ducts between the pancake windings 21. As depicted, the washers 31 are of progressively greater radial dimensions as the washers progress from the center of the coil outwardly in both directions. In FIG. 1, the washers 31 are shown as those associated with the rearward half of the coil, and the forward half would present the same appearance but in the opposite relationship. The insulating washers 31 each overlap the bent-over ends of vertical insulating wrapper sheets 33 disposed between the coil 19 and the core side portions to provide high dielectric strength therebetween. The wrapper sheets 33 from the outermost one progressively decrease in length in a radially inward direction, thereby grading the insulation to provide maximum insulation thickness between the magnetic core 17 and the pancake windings 21 at the point of highest potential relative to ground and progressively decreasing the insulation thickness as the potential of the pancake windings relative to ground decreases. Also provided are a plurality of relatively heavy impregnated laminated paper insulators 36 which are disposed between the magnetic core 19 and the pancake windings 21 and are also located on the bottom to provide an insulating bottom barrier. The laminated insulators 36 are separated by maple blocks 37 to provide passages or ducts for the circulation of the oil.

As previously mentioned, the entire shunt reactor 10 is immersed in insulating and cooling oil 14 contained within the tank 11. However, the assembled reactor 10 is subject to a dryout process prior to deaerated insulating and cooling oil 14 being pumped into the tank 11 to reduce the moisture content of the insulation for reducing the power factor to acceptable values, generally below 1%. This power factor value is carefully recorded and is provided with the records relating to the particular stationary induction apparatus such as the reactor 10. However, the chemical and physical properties of the oil used in the reactor is subject to gradual change during use. Thus, during the aging process the oil is affected by temperature, moisture and other materials with which the oil is in contact. Since oil tends to permit water which enters the reactor to separate and precipitate to the bottom of the tank, the integrity of the insulation dryness is affected.

To provide an improved method of determining the insulation dryness without the necessity of disconnecting the reactor from the power system with or without de-energizing the reactor apparatus, a moisture detector 40 is provided. As shown in FIG. 1, the moisture detector 40 is an integral part of the main insulation of the reactor 10. The moisture detector 40 indicates the state of dryness of the reactor insulation by means of power factor measurements. Such measurements may be taken easily and quickly and provide data which are more meaningful than tests made at the line terminals. To this end, planar conductive electrodes 41 and 42, such as metal foil or carbon paper, are laid and affixed to the laminated insulators 36 and preferably to representative insulators 38 and 39 which are separated from each other by at least one intervening insulator 43 to form a capacitor integral with the reactor insulation. In this arrangement, the electrodes 41 and 42 are placed in the bottom of the tank 11 where the precipitated water collects. With this arrangement and location, the electrodes are not sensitive to external stray magnetic or electric fields which are usually present. This is true because with the electrodes 41 and 42 located in the bottom of the tank 11 they are shielded from such fields.

In FIG. 4, the electrode 41 is shown in detail and its construction and arrangement is duplicated for the electrode 42. The electrode 41 comprises a sheet of carbon paper 46 having an area sufficiently large enough to provide good capacitance, preferably of 1000 picofarads. This will insure that the measurements will be representative. If the capacitance of the electrode is less than 500 picofarads, stray capacitance could affect the measurements taken.

The sheet carbon paper 46 has a preferred relative resistivity of 100 ohms per square centimeter so that the sheet carbon paper is a good conductor to handle the few milliamperes of the standard bridge measuring apparatus current. To collect the current from the sheet carbon paper electrode, a grid structure 47 of copper material is intimately secured to the sheet carbon paper electrode. A lead 48 is electrically connected to the collector grid 47. A kraft paper backing 49 serves as a reinforcing back cover, and a similar reinforcing top cover 51 of kraft paper is provided for the top cover of the electrode. The top and back covers 49 and 51 are in themselves not a part of the electrode but are provided to facilitate the handling of the electrode since the sheet carbon paper is relatively thin and ruptures easily. The electrode 42 is similar to the electrode 41 and has a lead 52 electrically connected to its associated collector grid. Leads 48 and 52 are brought out through insulated bushings to a terminal box 53 located on the upper portion of the tank on a side surface thereof.

With the arrangement described, it is only necessary to de-energize the reactor prior to making the tests. With the reactor de-energized, the protective ground connectors (not shown) from either the lead 48 or 52 is removed. Low power factor two-terminal measuring instruments, such as those normally used for transformers and bushings, including the 110 volt bridges, are suitable for making arrangements and are connected to leads 48 and 52. One such standard power factor measuring apparatus is manufactured by the Doble Company. Measurements are made from lead 48 with lead 52 grounded. The dissipation or power factor value obtained is compared to corresponding data made at the factory and contained in the test report which accompanies each reactor. Any sharp differences or adverse trends in the data obtained in the test from the data supplied from the factory will indicate the state of dryness of the insulation. This test measures the insulation dryness between the electrodes 41 and 42 and is usually the test that is made on a frequent period base.

However, if it should be desired to take a measurement of insulation dryness in other portions of the reactor device, other tests are capable of being made using three-terminal instruments. All tests capable of being made are listed in the following table:

| Test No. | Line On | Ground On | Guard On | Insulation Tested |
|---|---|---|---|---|
| 1 | 41 | 42 | Winding | 41 to 42 |
| 2 | 42 | Winding | 41 | 42 to Ground |
| 3 | 41 | Winding | 42 | 41 to Winding |
| 4 | Winding | 42 | 41 | Winding to Ground |

As previously mentioned, with electrode 41, which is nearest to the windings 21 connected to the high voltage line of the standard measuring apparatus, and with the electrode 42, which is furthest from the windings 21 connected to the ground line of the measuring apparatus, and the windings connected to the guard circuit of the measuring apparatus to eliminate the windings from the measurement procedure, a dissipation or power factor value indicating the relative dryness of the insulation between the two electrodes is measured.

In test No. 2, electrode 41, which is nearest to the windings 21, is connected to the guard circuit of the measuring apparatus, thereby removing it from the test. The electrode 42, which is furthest from the reactor windings 21 is connected to the high voltage line of the standard measuring apparatus; the windings 21 are connected to the ground line of the measuring apparatus. Under this condition the power factor value obtained indicates the relative dryness of the insulation between the electrode 42 and the bottom of the tank 11.

In test No. 3, the electrode 41, nearest the windings 21, is connected to the high voltage line of the measuring apparatus; the windings 21 are connected to the measuring apparatus ground line; and the electrode 42 furthest from the windings 21 is connected to the measuring apparatus guard circuit to remove this electrode from the test measurement. With this condition obtained, the power factor value obtained indicates the relative dryness of the insulation between the electrode 41 and the windings 21.

In test No. 4, the windings 21 are connected to the high voltage line of the standard measuring apparatus; the electrode 42 is connected to the ground line of the measuring apparatus; and the electrode 41 is connected to the guard circuit to remove it from the test measurement. With this condition obtained, the dissipation or power factor value obtained indicates the relative dryness of the insulation to the sides of the reactor or between the windings 21 and ground.

In FIGS. 2 and 3, a modified arrangement of the moisture detector is shown. The moisture detector 60 is bodily disposed in the lower bottom corner of the tank 11A and, thus, is located in the area of the high moisture accumulation. The detector 60 comprises a plurality of concentrically arranged insulator tubes 60 maintained in concentric spaced apart relationship by laminated insulator wood discs 61 and 62. A rod 63 coaxial with and extending through the detector receives a spring 64 and an adjusting nut 66. Thus, by adjusting the nut 66, tension against the spring 64 may be applied to hold the tube insulators 60 in concentric spaced apart relationship. A first tubular electrode 67 of cylindrical copper sheet is interposed in spaced apart relationship between the insulator tubes 60C and 60D. Another tubular electrode 68 is interposed in spaced apart relationship between insulator tubes 60D and 60E. Thus, the electrodes 67 and 68 are separated by the insulator tube 60D. The electrodes 67 and 68 are provided with leads 71 and 72, respectively, which are connected to a terminal box (not shown) similar to the box 53 in FIG. 1. The insulator tubes 60 are of an insulation material which is representative of the insulation utilized within the reactor 10A. The detector 60 makes it possible to retro-equip reactors that did not have a moisture detector as original equipment.

The embodiments of the invention in which an exclusive property or privilege is claimed are defined as follows:

1. In a method of determining the insulation dryness of an electrical reactor device immersed in oil contained in a tank which is at ground potential without de-energizing the reactor device comprising:
   providing a pair of spaced apart electrodes separated by at least one layer of representative insulation of the reactor device which is disposed adjacent to the bottom of the tank to form a capacitor;
   grounding the one electrode nearest to the windings of the reactor device;
   measuring the dissipation or power factor between the grounded and ungrounded electrodes to obtain a value; and,
   comparing the dissipation or power factor measured value obtained to similar dissipation or power factor data previously obtained on the representative or similar insulation of the reactor device of known dryness.

2. In a method of determining the insulation dryness of an electrical reactor device immersed in oil contained in a tank which is at ground potential comprising:
   providing a pair of spaced apart electrodes separated by at least one layer of representative insulation of the reactor device which is disposed adjacent to the bottom of the tank where precipitated water collects to form a capacitor;
   de-energizing the reactor device;
   grounding one of the electrodes;
   measuring the dissipation or power factor between the grounded electrode and the ungrounded electrode; and,
   comparing the dissipation or power factor measured value obtained to similar dissipation or power factor data previously obtained on the representative or similar insulation of the reactor device of known dryness to thereby determine the localized concentration of moisture in the insulation of the reactor device which is most likely to be the first to be contaminated.

3. In a method of determining the insulation dryness of a stationary induction device immersed in oil contained in a tank which is at ground potential;
   providing a pair of spaced apart sheet electrodes separated by at least one layer of representative insulation of the stationary induction device which is disposed adjacent the bottom of the tank where precipitated water collects to form a capacitor;
   de-energizing the stationary induction device;
   grounding one of the sheet electrodes;
   applying a selected power frequency voltage from a low voltage type of a power factor measuring apparatus which operates with substantially 110 volts to the other of the sheet electrodes;
   measuring the power factor between the sheet electrodes; and,
   comparing the measured power factor value obtained from the measuring apparatus to similar power factor data previously obtained on the representative or insulation of the stationary inductive device of known dryness to thereby determine the localized concentration of moisture in the insulation of the stationary induction device in the area where precipitated moisture collects in the tank.

4. In a method of determining the insulation dryness of the stationary induction device immersed in oil contained in a tank which is at ground potential comprising:

providing a pair of sheet electrodes in the structure of the induction device in the region of greatest moisture potential and separated by at least one layer of representative insulation of the induction device to form a capacitor;

de-energizing the induction device without disconnecting the device from a power system;

connecting the electrode furthest from the windings of the induction device to the ground line of a standard measuring apparatus;

connecting the winding of the inductor device to the guard circuit of the standard measuring apparatus to eliminate the windings of the induction device from the measurement;

connecting the other of the electrodes to the high voltage line of the measuring apparatus to determine the value of the power factor between the electrodes;

measuring the power factor between the sheet electrodes; and, comparing the measured power factor value obtained from the measuring apparatus to similar power factor data of the insulation of known dryness to thereby determine the localized concentration of moisture in the insulation between the sheet electrodes.

5. In a method of determining the insulation dryness of a stationary induction device immersed in oil contained in a tank which is at ground potential comprising:

providing a pair of sheet electrodes in the structure of the induction device in the region of the greatest moisture potentiality and separated by at least one layer of representative insulation of the induction device to form a capacitor integral with the insulation of the inductor device;

de-energizing the induction device;

connecting the windings of the induction device to the ground line of a standard measuring apparatus;

connecting the electrode nearest to the windings of the induction device to the guard circuit of the measuring apparatus to remove the windings from the measurement;

connecting the other of the electrodes to the high voltage line of the measuring apparatus to determine the power factor between the electrode and the bottom of the tank of the induction device;

measuring the power factor between the electrode connected to the high voltage line of the measuring apparatus and the bottom of the tank; and, comparing the measured power factor value obtained from the measuring apparatus to similar power factor data of the insulation of known dryness to thereby determine the localized concentration of moisture in the insulation of the induction device between the sheet electrode which is connected to the high voltage line of the measuring apparatus and the bottom of the tank.

6. In a method of determining the insulation dryness of a stationary induction device immersed in oil contained in a tank which is at ground potential comprising:

providing a pair of sheet electrodes in the structure of the induction device in the region of the greatest moisture potentiality and separated by at least one layer of representative insulation of the induction device to form a capacitor integral with the induction device insulation;

de-energizing the induction device;

connecting the windings of the induction device to the ground line of a standard power factor measuring apparatus;

connecting the electrode furthest from the windings of the induction device to the guard circuit of the measuring apparatus to remove it from the measurement;

connecting the other of the electrodes to the high voltage line of the measuring apparatus to measure the value of the power factor between the electrode and the windings;

measuring the power factor between the electrode that is connected to the high voltage line of the measuring apparatus and the windings of the induction apparatus; and, comparing the measured power factor value obtained from the measuring apparatus to similar power factor data of the insulation of known dryness to thereby determine the localized concentration of moisture in the insulation of the inductor device between the sheet electrode which is connected to the high voltage line of the measuring apparatus and the windings of the induction device.

7. In a method of determining the insulation dryness of a stationary induction device immersed in oil contained in a tank which is at ground potential comprising:

providing a pair of sheet electrodes in the structure of the induction device in the region of the greatest moisture potentiality and separated by at least one layer of representative insulation of the induction device to form a capacitor;

de-energizing the induction device;

connecting the sheet electrode nearest to the induction device windings to the guard circuit of a standard power factor measuring apparatus;

connecting the other sheet electrode to the ground line of the standard power factor measuring apparatus;

connecting the windings of the induction device to the high voltage line of the power factor measuring apparatus to determine the power factor value of the insulation between the windings of the induction device and ground at the sides of the induction device;

measuring the power factor between the windings of the induction device and ground at the sides of the induction device; and, comparing the measured power factor value obtained from the measuring apparatus to similar power factor data of the insulation of known dryness to thereby determine the localized concentration of moisture in the insulation between the windings of the inductor device and ground at the sides of the inductor device.

8. In a method of determining the insulation dryness of a stationary induction device immersed in oil contained in a tank which is at ground potential comprising:

providing a pair of sheet electrodes separated by at least one layer of representative insulation which is used in the induction device to form a capacitor;

locating the formed capacitor within the tank in a region of high moisture potential but apart from the induction device;

de-energizing the induction device;

connecting one of the electrodes to a ground line of a standard power factor measuring apparatus;

connecting the other of the electrodes to the guard circuit of the standard power factor measuring apparatus to remove it from the test measurement;

connecting the windings of the induction device to the high voltage line of the standard power factor measuring apparatus;

measuring the power factor between the electrodes; and, comparing the measured power factor value obtained from the measuring apparatus power similar powr factor data of the insulation of known dryness to thereby obtain the localized concentration of moisture in the insulation of the inductor device at the sides thereof between the windings of the inductor device and the sides of the tank which is at ground potential.

* * * * *

UNITED STATES PATENT OFFICE
CERTIFICATE OF CORRECTION

Patent No. 3,961,246            Dated June 1, 1976

Inventor(s) Michael W. Waterman and Samuel L. Foster

It is certified that error appears in the above-identified patent and that said Letters Patent are hereby corrected as shown below:

In Claim 3 column 6 line numbered 47, after "potential" the semicolon (;) should be deleted and a colon (:) should be inserted.

In Claim 8 column 10, line numbered 4 "power" (first occurance) should be deleted and ----to---- should be inserted.

In Claim 8, column 10, line numbered 4, "powr" (second occurance) should have been ---power----.

Signed and Sealed this

Fourteenth Day of September 1976

[SEAL]

Attest:

RUTH C. MASON
Attesting Officer

C. MARSHALL DANN
Commissioner of Patents and Trademarks